United States Patent [19]

Moore

[11] Patent Number: Plant 5,722

[45] Date of Patent: Apr. 22, 1986

[54] MINIATURE ROSE PLANT

[75] Inventor: Ralph S. Moore, 2519 E. Noble Ave., Visalia, Calif. 93277

[73] Assignee: Sequoia Nursery, Visalia, Calif.

[21] Appl. No.: 644,017

[22] Filed: Aug. 24, 1984

[51] Int. Cl.[4] ..... A01H 5/00

[52] U.S. Cl. ..... Plt./7

[58] Field of Search ..... Plt./7

*Primary Examiner*—Robert E. Bagwill

[57] ABSTRACT

The subject of the present disclosure is a new and distinct variety of miniature rose plant characterized primarily by the pink and white color blend of buds and flowers and further identified by the well foliaged symetrical plant.

1 Drawing Figure

The present invention relates to a new and distinct variety of hardy, dwarf, bush type rose plant of the miniature class; the variety being primarily characterized—as to novelty—by a unique blending of pink and white in both buds and flowers, the general color effect being pink.

The variety is further characterized by:

An abundance of bloom, with flowers borne singly or several to the stem in loose clusters.

Little or no fragrance.

A plant which is vigorous, of rounded somewhat spreading shape with semi-glossy small foliage with pointed leaflets; the buds and flowers being similar in form to Beauty Secret (miniature—not patented) but slightly larger in size.

The plant, which has a normal height of 12–14 inches or more, can easily be maintained at lesser height by occasional trimming.

A plant which grows and blooms satisfactorily both in greenhouse and outdoors; is good for growing in pots; and provides excellent garden decoration as well as cut flowers.

The present variety of miniature rose was originated by me at Sequoia Nursery located at Visalia, Calif., under conditions of careful control and observation, as a cross between Avandel (miniature—U.S. Plant Pat. No. 4,366) as the seed parent and Old Master (Floribunda—not patented), as the pollen parent.

Subsequent to origination of the variety I successfully asexually reproduced it at Sequoia Nursery, located as aforesaid, by budding as well as by cuttings; the reproductions having run true in all respects.

The color photograph illustrates the variety, including the foliage, buds and flowers.

Referring now specifically to the new and distinct variety of miniature rose plant, the following is a detailed description thereof in outline; all major color plate identifications being by reference to The British Colour Council Horticultural Colour Chart, except where common terms of color definition are employed.

Type: Hardy; dwarf; bushy; rounded; seedling; greenhouse; outdoors; cut flowers; garden decoration; potted plant.

Class: Miniature. Variety Name: MORbox (Commercial synonym: JEWEL BOX).

Flowers borne: Several together (3 to 5) but usually singly on slender, wirey stems.

Quantity of bloom: Abundant both outside and in greenhouse.

Bud:

*Peduncle.*—Medium to long; slender but sturdy; erect; medium to light green; hairs — numerous very short fuzz-like hairs.

*Before calyx breaks; size.*—Small. Form long; pointed with numerous soft, very short hairs and occasional foliaceous apendages on surface of bud; with foliaceous parts extending beyond the tip of the bud equal to one-half or more of its length.

*Color.*—Medium green (sometimes tinted bronze).

*As calyx breaks, color.*—Near white to pale pink. Opening: opens well in all weather.

Bloom:

*Size when fully open.*—Small, averaging about 40 mm ($1\frac{3}{4}''$).

*Petalage.*—Semi-double — Averaging about 18–20 petals, arranged regularly plus sometimes several petaloids.

*Form.*—High centered to cupped at first, becoming more open, with petals rolled loosely outward, and later at maturity open with petals remaining in similar shape and position. Petals tend to fold back at edges, giving each petal a "quilled" or pointed effect. Open flowers show stamens.

Petals: Fairly thick; satiny on inside and on outside surface.

*Shape.*—Outside petals, broad lanceolate with very short acute tip; intermediate — broad lanceolate, with very small acute tip; inside — lanceolate with acute or rounded tip.

Color: Newly opened flower from a plant grown in plastic greenhouse:

Outside petal:

*Outside surface.*—White or near white to pale pink (may show irregular areas or splashes of deeper pink).

*Inside surface.*—Near white on basal $\frac{1}{2}$ of petal blending into yellowish area at base; tip $\frac{1}{2}$ near Tyrian Rose 24/1 to 24/2 or lighter, with pink and white steaks in area where the colors blend together. Note: The pink color of inside surface of all petals may show a streaking or flecking which is a characteristic of this variety.

Intermediate petal:

*Outside surface.*—Similar to outside petal.

*Inside surface.*—Similar to outside petal.

Inner petal:

*Outside surface.*—Same as intermediate petal.

*Inside surface.*—Same as intermediate petal.

*General color effect; newly opened flowers.*—Color blending of pink shades.

*Three days open.*—Color similar to newly opened flowers but blended or shaded darker pink.

*Behavior.*—Opens well in all weather. Spent petals drop off.

*Flower longevity* (*June* 1984).—Plant in pot 6–8 days longer. Cut flowers at living room temperature 4–5 days.

Reproductive organs:

*Stamens.*—Abundant, arranged regularly about pistils.

*Filaments.*—Varying length, medium to long, yellow.

*Anthers.*—Well formed; yellow.

*Pollen.*—Abundant amount.

*Pistils.*—Average number.

*Styles.*—Fairly even; medium length; bunched; color — pale pinkish.

*Stigmas.*—Pale yellowish.

*Ovaries.*—All enclosed in calyx.

*Hips.*—Some.

*Sepals.*—Permanent; spear shaped; recurved.

*Seed.*—Few or none.

Foliage:

*Leaves.*—Compound of five leaflets (sometimes 3 or 7). Size — Small; leathery; semi-glossy.

*Leaflets.*—Shape: broad lanceolate; eliptical; apex acute; base rounded or rounded acute. Margin serrate. Color: Medium green; new growth — reddish or bronze. Rachis: Medium strength; upper side may have a few tiny short hairs or prickles, grooved; underside — several small hooked thorns and usually no hairs or tiny prickles. Stipules: Medium long; narrow to medium width; short length narrow points which turn out usually at about 45 degrees.

Growth:

*Habit.*—Dwarf; bushy; rounded; much branched.

*Growth.*—Free vigorous; internodes short.

*Canes.*—Medium; slender; sturdy.

*Main stems.*—Color; medium green.

*Thorns.*—Average; slender; straight, inclined slightly downward; color; brown. Prickles — few or none; hairs — none.

*Branches.*—Color: light to medium green. Thorns: average; medium length; slender; nearly straight, inclined slightly downward. Medium to short oval base. Prickles: few or none. Hairs: none.

*Young shoots.*—Color: light to medium green (reddish outdoors). Thorns; average, slender; straight, inclined slightly downward; color — greenish (or bronzy).

The miniature rose plant and its flowers as herein described may vary in slight detail due to climatic, soil and cultural conditions under which the variety may be grown; the present description being of the variety as grown at Visalia, Calif.

The following is claimed:

1. A new and distinct variety of miniature rose plant of hardy, dwarf, bushy, rounded, much branched habit substantially as illustrated and described, characterized by buds and flowers which are a blending of pink and white (sometimes with darker shading) with the reverse being white or near white, the buds and flowers resembling Beauty Secret (miniature—not patented) in shape but slightly larger in size; and further characterized by a plant which is vigorous and compact, easy to propagate from soft wood cuttings or by budding, with an abundance of flowers borne singly or several to the stem in loose clusters.

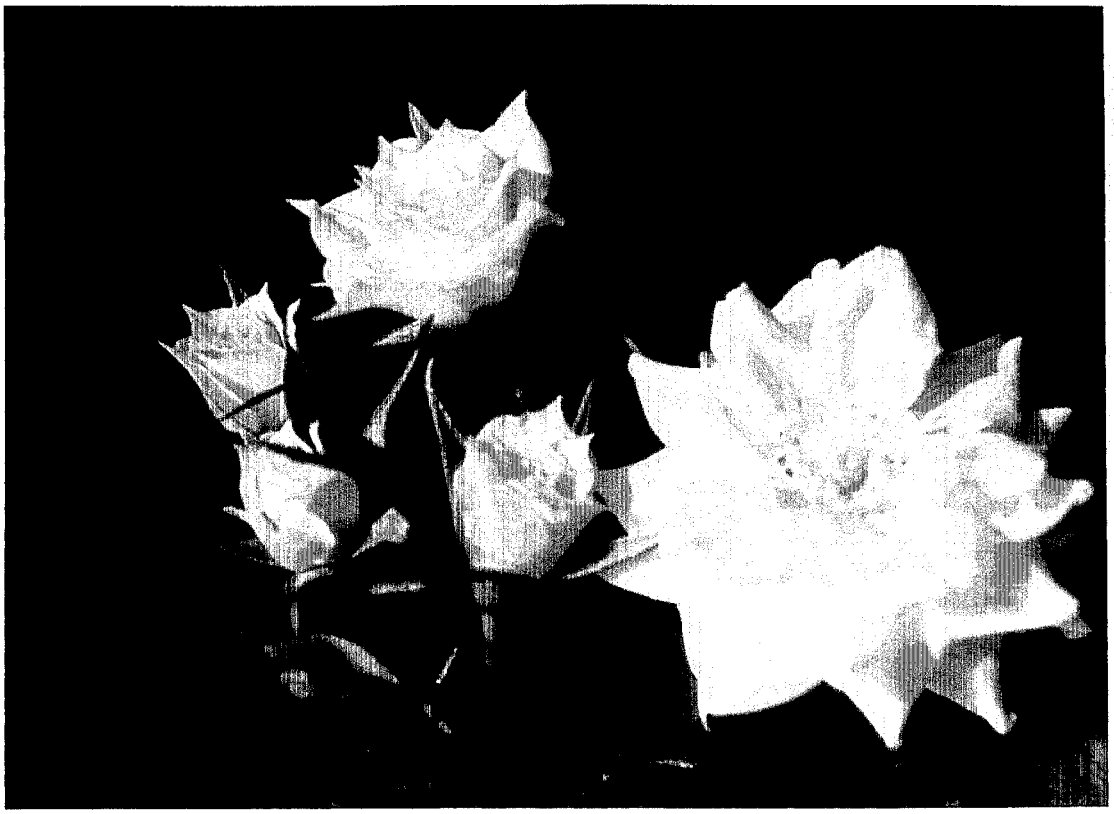

* * * * *